(12) United States Patent
McEwen et al.

(10) Patent No.: US 7,771,453 B2
(45) Date of Patent: Aug. 10, 2010

(54) OCCLUSION DETECTOR FOR DUAL-PORT SURGICAL TOURNIQUET SYSTEMS

(76) Inventors: James A. McEwen, c/o Western Clinical Engineering Ltd. Suite 207 - 1099 West 8th Avenue, Vancouver, British Columbia (CA) V7G 1S9; Michael Jameson, c/o Western Clinical Engineering Ltd. Suite 207 - 1099 West 8th Avenue, Vancouver, British Columbia (CA) V7G 1S9

( * ) Notice: Subject to any disclaimer, the term of this patent is extended or adjusted under 35 U.S.C. 154(b) by 1480 days.

(21) Appl. No.: 11/095,981

(22) Filed: Mar. 31, 2005

(65) Prior Publication Data

US 2006/0224181 A1    Oct. 5, 2006

(51) Int. Cl.
*A61B 17/00* (2006.01)
*A61B 5/02* (2006.01)

(52) U.S. Cl. .................... 606/203; 600/490
(58) Field of Classification Search ......... 600/490–500; 606/201–203; 601/148–152
See application file for complete search history.

(56) References Cited

U.S. PATENT DOCUMENTS

| | | | |
|---|---|---|---|
| 3,892,229 A | 7/1975 | Taylor |
| 4,013,069 A | 3/1977 | Hasty |
| 4,326,416 A | 4/1982 | Fredberg |
| 4,469,099 A | 9/1984 | McEwen |
| 4,479,494 A | 10/1984 | McEwen |
| 4,520,819 A | 6/1985 | Birmingham |
| 4,635,635 A | 1/1987 | Robinette-Lehman |
| 5,254,087 A | 10/1993 | McEwen |
| 5,316,002 A | 5/1994 | Jackson |
| 5,352,195 A | 10/1994 | McEwen |
| 5,439,477 A | 8/1995 | McEwen |
| 5,445,144 A | 8/1995 | Wodicka |
| 5,454,831 A | 10/1995 | McEwen |
| 5,556,415 A | 9/1996 | McEwen |
| 5,575,762 A | 11/1996 | Peeler |

(Continued)

OTHER PUBLICATIONS

International Search Report and Written Opinion; CIPO, Jul. 13, 2006; in corresponding PCT App CA2006/000473; 7 pages.

*Primary Examiner*—Charles A Marmor, II
*Assistant Examiner*—Christian Jang
(74) *Attorney, Agent, or Firm*—Hancock Hughey LLP (57) ABSTRACT

A occlusion detector for a dual-port surgical tourniquet system comprises: a tourniquet cuff for encircling a patient's limb and including an inflatable portion that communicates pneumatically with a first cuff port and that communicates pneumatically with a second cuff port independently of the first cuff port; a tourniquet instrument that is releasably connectable to the first and second cuff ports to establish first and second pneumatic passageways between the tourniquet cuff and the tourniquet instrument, wherein the tourniquet instrument includes pressure sensing means communicating with the first pneumatic passageway for producing an indication of the pressure in the cuff over a time period suitably long for the performance of a surgical procedure, pressure regulation means communicating with the second pneumatic passageway for regulating the pressure in the cuff near a reference pressure level, and an occlusion detector for introducing a pneumatic pressure pulse into the first pneumatic passageway during an occlusion detection time period, for monitoring the pressure in the second pneumatic passageway during the occlusion detection time period, and for producing an occlusion alarm if a fluctuation of pressure in the second pneumatic passageway is not detected within the occlusion detection time period.

11 Claims, 2 Drawing Sheets

U.S. PATENT DOCUMENTS

| | | |
|---|---|---|
| 5,584,853 A | 12/1996 | McEwen |
| 5,607,447 A | 3/1997 | McEwen |
| 5,649,954 A | 7/1997 | McEwen |
| 5,681,339 A | 10/1997 | McEwen |
| 5,741,295 A | 4/1998 | McEwen |
| 5,855,589 A | 1/1999 | McEwen |
| 5,911,735 A | 6/1999 | McEwen |
| 5,931,853 A | 8/1999 | McEwen |
| 5,935,146 A | 8/1999 | McEwen |
| 6,905,456 B1 * | 6/2005 | Brunner et al. ............... 600/16 |
| 7,485,131 B2 * | 2/2009 | Hovanes et al. ............. 606/202 |

\* cited by examiner

OCCLUSION DETECTOR FOR DUAL-PORT SURGICAL TOURNIQUET SYSTEMS

FIELD OF THE INVENTION

This invention pertains to pneumatic tourniquet systems commonly used for stopping arterial blood flow into a portion of a surgical patient's limb to facilitate the performance of a surgical procedure, and for facilitating intravenous regional anesthesia. In particular, this invention pertains to a pneumatic tourniquet system that includes a tourniquet instrument and a tourniquet cuff having an inflatable portion and two separate pneumatic ports for establishing two separate pneumatic passageways between the tourniquet instrument and the cuff.

BACKGROUND OF THE INVENTION

A typical surgical tourniquet system of the prior art includes a tourniquet cuff for encircling a patient's limb at a desired location, a tourniquet instrument, and flexible tubing connecting the cuff to the instrument. In some surgical tourniquet systems of the prior art, the tourniquet cuff includes an inflatable portion, and the inflatable portion of the cuff is connected pneumatically through one or two cuff ports by flexible plastic tubing to a tourniquet instrument that includes a pressure regulator to maintain the pressure in the inflatable portion of the cuff, when applied to a patient's limb at a desired location, at a pressure above a minimum pressure required to stop arterial blood flow past the cuff during a time period suitably long for the performance of a surgical procedure. Many types of such pneumatic surgical tourniquet systems have been described in the prior art, such as those described by McEwen in U.S. Pat. No. 4,469,099, U.S. Pat. No. 4,479,494, U.S. Pat. No. 5,439,477 and by McEwen and Jameson in U.S. Pat. No. 5,556,415 and U.S. Pat. No. 5,855,589. Some additional representative dual-port tourniquet cuffs of the prior art, suitable for use as elements of dual-port surgical tourniquet systems, are described in U.S. Pat. No. 4,635,635, U.S. Pat. No. 5,454,831, U.S. Pat. No. 5,439,477, U.S. Pat. No. 5,741,295 and U.S. Pat. No. 5,649,954.

To achieve better overall safety and performance, and in particular to achieve greater speed and accuracy in controlling the pressure in the tourniquet cuff, some advanced tourniquet systems include tourniquet cuffs that have two separate pneumatic cuff ports, so that two separate pneumatic passageways can be established between the inflatable portion of the cuff and the tourniquet instrument, by separately connecting flexible plastic tubing between each port and the instrument. Such systems are often called dual-port tourniquet systems. In one such dual-port tourniquet system of the prior art, described in U.S. Pat. No. 4,469,099, the pneumatic pressure regulation elements within the tourniquet instrument communicate pneumatically with the inflatable portion of the cuff through one port, and a pressure sensor within the tourniquet instrument communicates pneumatically with the inflatable portion of the cuff through the second port. This configuration enables more accurate sensing, monitoring and regulation of the actual pressure in the inflatable portion of the cuff that encircles the patient's limb, in comparison to single-port tourniquet systems.

In a typical single-port tourniquet system of the prior art, the tourniquet cuff has only one port and only one pneumatic passageway is established between the tourniquet cuff and the instrument. The cuff pressure must be sensed indirectly, through the same tubing and port that is used to increase, decrease and regulate the pressure in the cuff during surgery. As a result, in such a single-port tourniquet system of the prior art, the accuracy and speed of pressure regulation, and the accuracy of the sensed cuff pressure, are affected by the pneumatic flow resistance within the single port and within the flexible plastic tubing that pneumatically connects the port and cuff to the tourniquet instrument.

The increased accuracy possible with dual-port surgical tourniquet systems of the prior art is important for safety in surgery because of the well recognized importance of regulating the actual pressure in the tourniquet cuff near the minimum pressure that will reliably stop blood flow into the limb distal to the cuff during surgery: Higher tourniquet pressures are associated in the medical literature with higher risks of injury to the nerves and soft tissue of the patient's limb and other hazards, and lower tourniquet pressures may allow the flow of arterial blood past the cuff and into the limb and surgical field, thus complicating the surgery, extending the duration of surgery, and leading to congestion of the limb and other hazards.

The increased accuracy of pressure regulation that is possible with dual-port tourniquet systems facilitates increased accuracy in the determination of the minimum effective tourniquet pressure needed for a specific patient and surgical procedure as described by McEwen in U.S. Pat. No. 5,439,477. The greater accuracy of pressure regulation possible with dual-port tourniquet systems also allows such systems to respond more rapidly, more accurately and more safely to changes associated with movement of the patient's limb and cuff during surgery, and to changes associated with switching between cuffs for bilateral limb surgery, or for intravenous regional anesthesia. Dual-port tourniquet systems also facilitate rapid, accurate and safe adaptation to certain physiologic changes of the patient during surgery, as described for example in U.S. Pat. No. 4,479,494, and facilitate faster, more accurate and safer responses to changes in effective venous pressure in the limb distal to the cuff associated with the injection of anesthetic agents for intravenous regional anesthesia, as described for example in U.S. Pat. No. 5,254,087.

One hazard associated with all pneumatic surgical tourniquet systems is the possible occlusion, or blockage, of the pneumatic passageway between tourniquet instrument and cuff, or within the cuff itself. In many surgical procedures, the pressure regulator is located remotely from the patient, necessitating the use of long and flexible plastic tubing extending from the instrument and around and between equipment and staff to the cuff applied to the patient. Also, the ports of sterile disposable tourniquet cuffs are often long and soft and flexible, to allow the ports to be easily positioned away from the sterile surgical field, to minimize obstruction of the surgical field, and to allow the connection of the sterile ports to non-sterile tubing to be done outside of the surgical field. As a result, it is possible that the tubing or the port may become occluded for example by bending, kinking or pinching.

Also, it is recognized in the prior art that occlusions may occur within the inflatable portion of tourniquet cuff itself, thereby preventing the tourniquet cuff from effectively and uniformly applying pressure to the limb as intended. Some tourniquet cuffs of the prior art have specifically recognized and addressed this hazard in the design and manufacture of the inflatable portion of the cuffs and their associated ports. In general, if any occlusions occur in the tubing, cuff ports or inflatable portion of the cuff and are not promptly detected and remedied, the result may be hazardous for the patient.

The occlusion hazard is most apparent in certain single-port tourniquet systems of the prior art, in which any occlusion of the single port or tubing between the instrument and tourniquet cuff may prevent the tourniquet instrument from sensing and regulating the pressure in the cuff. Thus the actual pressure in the cuff may decrease substantially below the desired tourniquet pressure to a level where the cuff is completely depressurized, or the actual pressure may increase substantially above the desired tourniquet pressure, without any indication to the surgical staff and without any audiovisual alarms being activated to alert the staff. In effect, the monitoring and regulation of cuff pressure from the tourniquet instrument stops at the location of the occlusion. Such low or high pressures in the tourniquet cuff may be hazardous to the patient, for reasons indicated above.

Apparatus for detecting occlusions in both single-port and dual-port surgical tourniquet systems has been described in the prior art by McEwen and Jameson in U.S. Pat. No. 5,681,339 and U.S. Pat. No. 5,935,146. The apparatus and related method are based on an adaptation of the principle of acoustic reflectometry for pneumatic tourniquets: A brief pneumatic pressure pulse is periodically introduced from the tourniquet instrument into the pneumatic tubing connected to the cuff, and the instrument then analyzes reflections arising from pressure pulse which occur when the pulse encounters a change in the cross-sectional area of the pneumatic passageway as the pulse propagates along the passageway.

The apparatus and method of McEwen and Jameson described in U.S. Pat. No. 5,681,339 and U.S. Pat. No. 5,935,146 has been implemented in some commercially available single-port tourniquet systems of the prior art. However, there are a number of significant limitations. First, for implementation, additional components and higher resolution components must be included within such single-port tourniquet instruments, resulting in additional cost. Second, to be effective, the apparatus and method of McEwen and Jameson requires that the flexible plastic tubing between the tourniquet instrument and the cuff port have a fixed tubing length and a constant cross-sectional area, and requires that the cuff port connecting the tubing to the inflatable portion of the cuff also have a similar cross-sectional area to the flexible tubing that connects the instrument to the cuff port. Both of these requirements limit the general utility of the apparatus and method because in general it would be more useful to allow occlusion detection in tubing and in cuff ports having different lengths, diameters and cross-sectional areas. Another limitation of the apparatus and method of McEwen and Jameson is that it cannot reliably detect occlusions within the inflatable portion of a cuff, and it would be desirable to have an occlusion detector that could do so, because such occlusions within the cuff can occur in practice. A related limitation is that the apparatus and method may erroneously indicate occlusions if very small cuffs such as pediatric tourniquet cuffs are used, especially if such cuffs are wrapped tightly around a patient's limb. In such cases, the effective inflation volume of the cuff is very small, and as a result an occlusion at the cuff may erroneously be indicated. Still another limitation is that, to be effective, the apparatus and method of McEwen and Jameson requires known and fixed specifications for any pneumatic valves inserted between the tourniquet instrument and cuff. In practice this requirement can present a problem because additional pneumatic valves having unknown specifications may be inserted by surgical staff between the cuff and instrument to facilitate bilateral limb surgery and intravenous regional anesthesia (Bier block anesthesia).

The apparatus and method described by McEwen and Jameson in U.S. Pat. No. 5,681,339 and U.S. Pat. No. 5,935,146 have not been implemented in any commercial dual-port tourniquet systems of the prior art, primarily because of increased complexity and cost. The additional cost of implementation in a dual-port system would be approximately double the cost of implementation in a single-port system, because each tube and connected port must be separately monitored for occlusions.

In the prior art, an apparatus specifically intended for detecting occlusions in some dual-port surgical tourniquet systems has been described by Birmingham and Manes in U.S. Pat. No. 4,520,819. The apparatus employs a pair of pressure differential switches in the instrument, connected anti-parallel between the pneumatic passageways connecting the instrument to the dual-port cuff, which activate an occlusion alarm when a pressure differential develops across them. The underlying assumption is that a pneumatic occlusion will eventually result in a pressure differential that is sufficiently large to be detected within the instrument. However, inherent limitations in such apparatus for detecting occlusions have prevented it from being incorporated into commercial dual-port tourniquet systems of the prior art.

A basic limitation is that the apparatus of Birmingham et al. cannot detect an occlusion that is not associated with a pressure differential. Significantly, it cannot detect a simultaneous kinking, pinching and blockage of both tubes connecting dual-port cuffs to the instrument, as can occur during surgery. In such a case, there may be no pressure differential in the passageways between the instrument and the kink or blockage, and thus no alarm. In such a circumstance, the dual-port cuff could be completely disconnected from the tubing without an occlusion alarm being activated.

Another important limitation of the apparatus of Birmingham et al. is that inherent flow resistance within the flexible plastic tubing, ports and cuff may produce a significant pressure differential during inflation or deflation of the cuff, thus activating false occlusion alarms. A related limitation is that, if an effort is made to avoid such false alarms by raising the level of pressure differential at which an occlusion alarm is activated, then the detection of an actual occlusion may be delayed or prevented, leading to a hazardously high or low pressure in the tourniquet cuff applied to the patient. Yet another limitation of the apparatus of Birmingham et al. is that it requires the inclusion of additional electronic components and pneumatic connections within the dual-port tourniquet instrument, increasing costs and introducing potential secondary hazards associated with malfunctions of such components that may be difficult to detect.

There is a need for an improved occlusion detector for dual-port surgical tourniquet systems that overcomes the above-described problems and limitations of occlusion detectors of the prior art. Ideally, an occlusion detector would not require the addition of special components, circuitry or pneumatic connections within a dual-port tourniquet instrument, and thus would not increase instrument costs and would not introduce secondary hazards associated with potential malfunctions of such additional components, circuitry and pneumatic connections. An occlusion detector should promptly and reliably detect occlusions in the tubing, in the cuff ports, and within the inflatable portion of the dual-port cuff itself, regardless of whether the cuff is sterile or reusable, regardless of the size, shape, composition and length of the cuff ports, and regardless of the type of cuff port connectors. Also, an occlusion detector should reliably detect occlusions within inflatable portions of dual-port tourniquet cuffs that have a wide variety of shapes, compositions and sizes, and thus a wide variety of inflatable cuff volumes when applied to a limb.

An occlusion detector for dual-port tourniquet systems should detect occlusions in only one tube or connected port, and should also detect simultaneous occlusions of both cuff ports or both connected tubes. To be generally useful, an occlusion detector for dual-port tourniquet systems should not require that the lengths, sizes and shapes of tubing be known in advance for reliable operation, nor should it unduly limit the types of pneumatic valves that may be inserted between cuff and instrument to facilitate bilateral limb surgery and intravenous regional anesthesia. The present invention addresses the need for an improved occlusion detector for dual-port surgical tourniquet systems.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
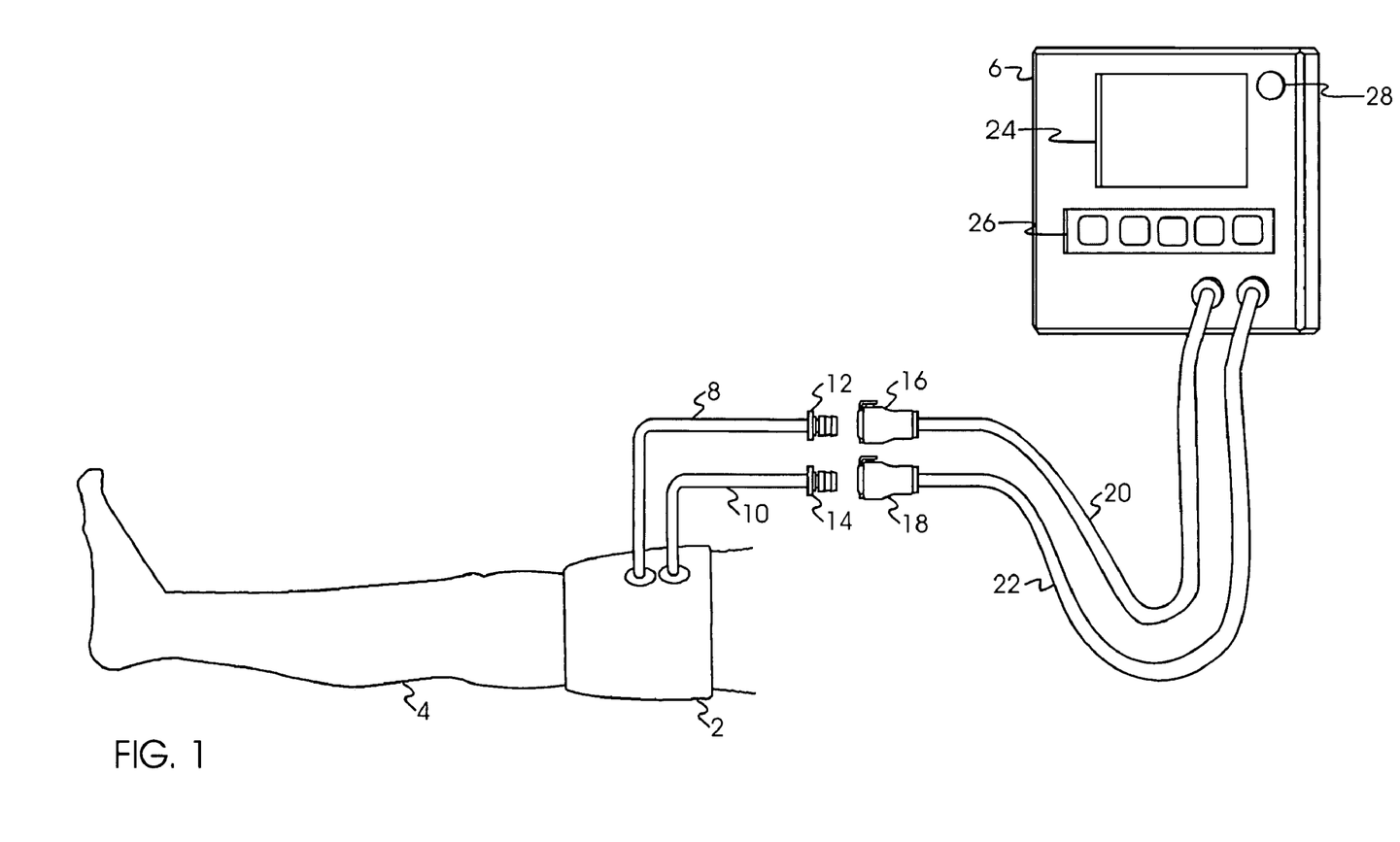
FIG. 1 is a pictorial representation of the preferred embodiment in a surgical application.

FIG. 1 shows pressurizing cuff 2 applied to patient limb 4 and pneumatically connectable to instrument 6. The inflatable portion of pressurizing cuff 2 has two separate pneumatic connections and is generally similar in design and construction to the cuffs described by McEwen in U.S. Pat. No. 5,741,295, U.S. Pat. No. 5,649,954, U.S. Pat. No. 5,484,831 and by Robinette-Lehman in U.S. Pat. No. 4,635,635. Cuff 2 is adapted for use in a sterile surgical field in an operating room environment by being formed of materials that can withstand, and that can be sterilized by, techniques normally used to sterilize medical devices to a level of sterility that allows them to be safely used within a sterile surgical field.

Cuff 2 is a dual-port cuff, and separate pneumatic passageways to the inflatable portion of cuff 2 are provided by cuff port 8 and cuff port 10 so that each passageway is independent of the other. In FIG. 1, cuff port 8 and cuff port 10 are of sufficient length to allow pneumatic connections to cuff 2 to be made outside of a sterile surgical field. Cuff port 8 and 10 are fitted with male locking connectors 12 and 14 (DSM2202, Colder Products Company, St. Paul, Minn.) respectively, and mate to form releasable pneumatic connections with female locking connectors 16 and 18 (PMC1704, Colder Products Company, St. Paul, Minn.). For clarity, the connectors illustrated in FIG. 1 are shown disconnected. In the following description of the preferred embodiment the connectors are mated and form part of the pneumatic passageways between instrument 6 and cuff 2. Pneumatic connections from instrument 6 to cuff 2 are made by flexible plastic tubing 20 and 22, which are fitted with female locking connectors 16 and 18 respectively.

As can be seen in FIG. 1, instrument 6 has a user interface consisting of graphic display panel 24, keypad 26, and visual alarm indicator 28. Display panel 24 is employed for the selective display of any of the following alphanumeric information: actual cuff pressures as measured by instrument 6; reference or "set" cuff pressure levels; alarm reference "limits" or values; alphanumeric alarm messages describing detected alarm conditions and other information required for the operation of instrument 6.

Keypad 26 controls the operation of instrument 6. Keypad 26 has an "inflate" key to initiate the inflation of cuff 2, a "deflate" key to initiate the deflation of cuff 2, and other keys to permit the user of instrument 6 to adjust the cuff pressure reference level and set inflation time alarm limits.

Visual alarm indictor 28 is a bright red light emitting diode (LED), which is activated by instrument 6 in response to detected alarm conditions. Instrument 6 also signals the presence of an alarm condition by generating an audible tone to further alert the user to the presence of an alarm condition and displays alarm text messages describing the alarm condition on display panel 24. An example of a detected alarm condition that requires the user's attention is an occlusion of tubing 20 or tubing 22. Other alarm conditions that are indicated by the illumination of visual alarm indicator 28 are described further below.

Figure 2:
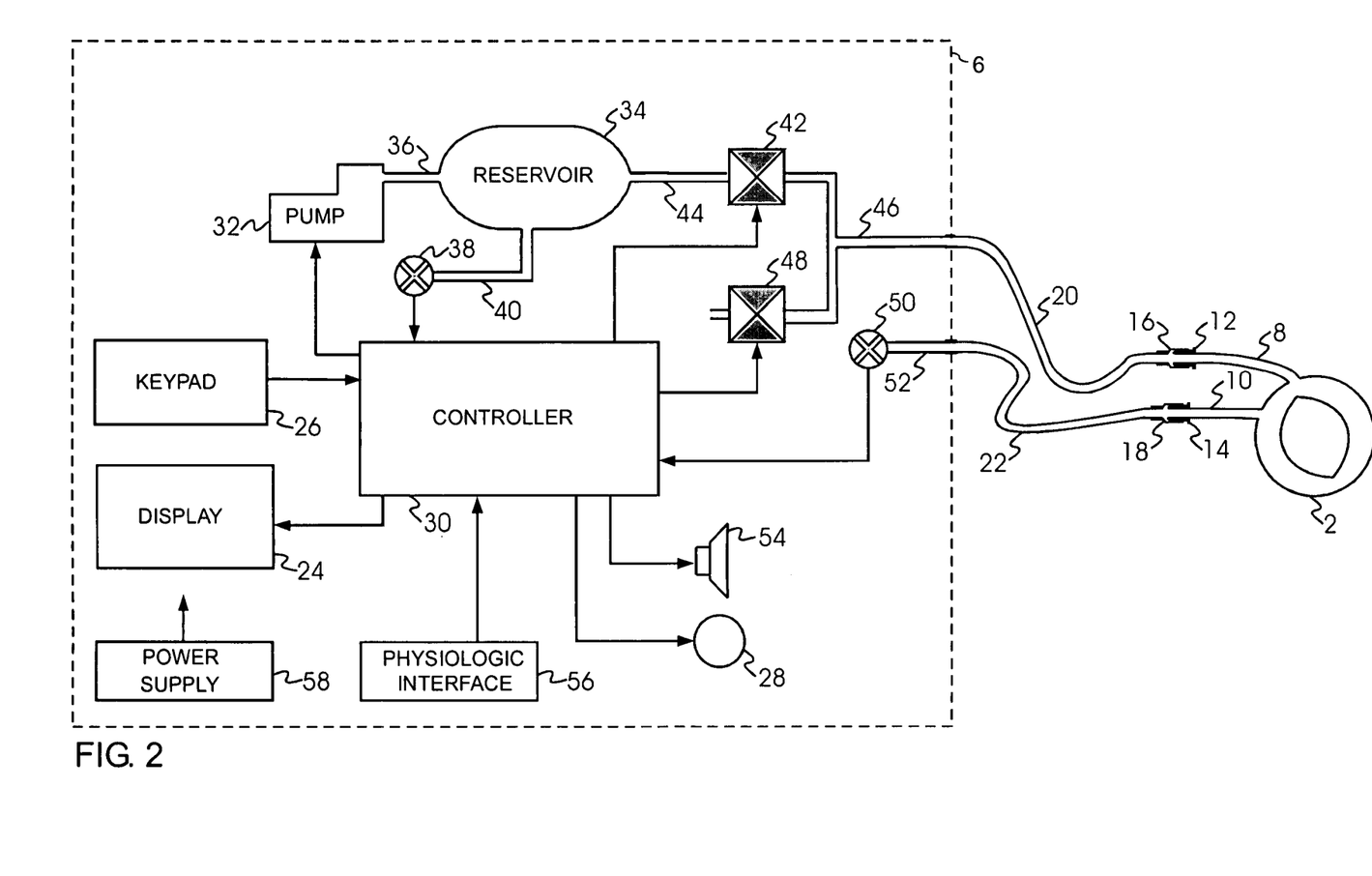
FIG. 2 is a block diagram of the preferred embodiment.

Referring to the block diagram of instrument 6 shown in FIG. 2, controller 30 comprises a microcontroller (MC68HC16Z1, Freescale Semiconductor, Austin, Tex.) associated memory and control software, analog and digital peripheral interface circuitry, and other necessary support components.

As shown in FIG. 2, pneumatic pump 32 (KNF Neuberger, Inc., Trenton, N.J.) is pneumatically connected to reservoir 34 by tubing 36. In response to control signals from controller 30, pump 32 operates to pressurize reservoir 34. Reservoir pressure transducer 38 is pneumatically connected by tubing 40 to reservoir 34 and generates a reservoir pressure signal. The reservoir pressure signal is communicated to controller 30. Controller 30 acts to maintain the pressure in reservoir 34 near a reservoir pressure reference level. Controller 30 sets the reservoir pressure reference level to a pressure above the cuff pressure reference level set by the user of instrument 6; the reservoir reference pressure level is set to a level significantly greater than the cuff pressure reference level, typically 100 mmHg. Controller 30, in response to the reservoir pressure reference level and the reservoir pressure signal, activates pump 32 to maintain the value of the reservoir pressure signal near the cuff reservoir pressure reference level.

Inflation valve 42 (EVO-3-12V Clippard Instrument Laboratory, Cincinnati, Ohio) is configured as a two position normally closed valve. One side of the valve is pneumatically connected via tubing 44 to reservoir 34 the other side of the valve is connected to cuff 2 via the pneumatic passageway formed by manifold 46, tubing 20, connectors 16 and 12 and cuff port 8. When energized by controller 30, inflation valve 42 moves to the open position and allows pressurized gas to flow from reservoir 34 to cuff 2, thereby increasing the pressure of gas in the inflatable portion of cuff 2.

Deflation valve 48 (EVO-3-12V Clippard Instrument Laboratory, Cincinnati, Ohio) is configured as a two position normally closed valve. One side of the valve is pneumatically connected to cuff 2 via the pneumatic passageway formed by manifold 46, tubing 20, connectors 16 and 12 and cuff port 8, the other side is open to atmosphere. When energized by controller 30, deflation valve 48 moves to the open position and allows pressurized gas to flow from cuff 2 to atmosphere, thereby decreasing the pressure of gas in the inflatable portion of cuff 2.

In the preferred embodiment the inflation and deflation valves share a common pneumatic connection with a port of cuff 2. It will be appreciated that other configurations of the inflation and deflation valves may be employed. For example, it may be desirable to have the inflation valve communicate separately with one port of cuff 2 and to have the deflation valve communicate separately with the other port of cuff 2. This possible configuration may be desirable if the inflatable portion of cuff 2 includes a pressure transducer that communicates wirelessly with instrument 6 to directly indicate the pressure in cuff 2.

Cuff pressure transducer 50 is pneumatically connected to cuff 2 via the pneumatic passageway formed by tubing 52, tubing 22, connectors 18 and 14 and cuff port 10 and generates a cuff pressure signal which is communicated to controller 30. The separate independent pneumatic connection between the inflatable portion of cuff 2 and transducer 50 provides for an accurate indication of the pressure of gas within cuff 2. Controller 30 is able to resolve changes in the cuff pressure signal as small as 0.15 mmHg.

As noted above, controller 30 will, in response to generated alarm signals, alert the user of an alarm condition by activating visual alarm indicator 28 and producing audible tones.

Speaker 54 is connected to controller 30, electrical signals having different frequencies to specify different alarm signals and conditions are produced by controller 30 and converted to audible sound by loudspeaker 54.

Physiologic interface 56 provides a means for controller 30 to interface with and receive information from physiologic sensors. Controller 30 may, if desired, automatically adjust the cuff pressure reference level in response to information received from physiologic sensors via physiologic sensor interface 56. For example, the cuff pressure reference level may be automatically adjusted by controller 30 in response to a sensor for determining the minimum effective cuff pressure within cuff 2 required for occluding blood flow past cuff 2. Also, controller 30 may automatically adjust the cuff pressure reference level in response to changes in venous pressure, which may occur during intravenous regional anesthesia, and in response to changes in other physiologic parameters such as blood pressure.

Power supply 58 connects to an external AC supply and provides regulated DC power for the normal operation of all electronic components of instrument 6. Power supply 58 may also include a battery to enable instrument 6 to continue to operate in the absence of an external AC supply.

A user of instrument 6 may use keypad 26 to select a cuff pressure reference level, this is the pressure of gas that instrument 6 will attempt to maintain in the inflatable portion of cuff 2 when cuff 2 is inflated. Controller 30 will generate high or low-pressure alarm signals if the pressure in cuff 2 cannot be maintained near the selected cuff pressure reference level. If the value of the cuff pressure signal exceeds the cuff pressure reference pressure level by 15 mmHg a high-pressure alarm signal will be generated by controller 30. If the value of the cuff pressure signal falls below the cuff pressure reference level by 15 mmHg a low-pressure alarm signal will be generated by controller 30.

When controller 30 detects that the "inflate" key on keypad 26 has been depressed by a user of instrument 6, controller 30 operates to inflate cuff 2 to a pressure near the selected cuff pressure reference level and to then regulate the pressure in cuff 2 near the value set by cuff pressure reference level.

To inflate and regulate the pressure in cuff 2, controller 30 includes a pressure regulator; the operation of the control algorithm for the pressure regulator is described below. At regular predetermined regulation intervals of 40 ms, controller 30 computes the value of a pressure error signal. The pressure error signal is the difference between the cuff pressure reference level and the cuff pressure signal. Controller 30 uses the pressure error signal as a term in a proportional integral control algorithm to calculate activation time intervals for inflation valve 42 and deflation valve 48. To increase the gas pressure in cuff 2 when the cuff pressure signal is below the cuff pressure reference level, the activation time interval for deflation valve 48 is set to zero and the activation time interval for inflation valve 42 is proportional to the magnitude of the pressure error signal and the integral of the pressure error signal. To decrease the gas pressure in cuff 2 when the cuff pressure signal is above the cuff pressure reference level, the activation time interval for inflation valve 42 is set to zero and the activation time interval for deflation valve 48 is proportional to the magnitude of the pressure error signal and the integral of the pressure error signal. Controller 30 limits the maximum valve activation time intervals of valve 42 and valve 48 to the regulation interval time (40 ms). It will be appreciated by those skilled in the art that alternate pressure regulation algorithms could be employed to control the activation of inflation valve 42 and deflation valve 48 in response to a cuff pressure signal and a cuff pressure reference level, or that proportional valves could be used instead of the valves used in the preferred embodiment.

In order to correctly regulate the pressure of gas in cuff 2 at a pressure near the cuff pressure reverence level and correctly indicate over and under pressure alarm conditions, controller 30 must have available an accurate indication of the pressure within the inflatable portion of cuff 2. In the preferred embodiment the accurate measurement of the pressure of gas in cuff 2 is facilitated by cuff pressure transducer 50 and the direct pneumatic connection between the inflatable portion of cuff 2 and transducer 50. The connection between the inflatable portion of cuff 2 and transducer 50 is made by tubing 52, flexible plastic tubing 22, connectors 18 and 14, and cuff port 10. In clinical use, tubing 22 or cuff port 10 may become inadvertently kinked and occluded in the operating room environment.

When an occlusion of the pneumatic connection between transducer 50 and cuff 2 occurs, the pressure regulator will respond to the pressure of the gas trapped in the tubing between the site of the occlusion and transducer 50 and will be no longer responsive to the actual pressure of gas within the inflatable portion of cuff 2. If the occlusion is not detected and the pressure regulator permitted to continue to affect the cuff pressure, the pressure regulator may over or under pressurize cuff 2 as the value of the cuff pressure error signal, described above, is no longer indicative of the pressure difference between the actual cuff pressure and the cuff pressure reference level as set by the user. Also, any change in the pressure of gas within cuff 2 during the time that an occlusion in tubing 22 or cuff port 10 persists will not be detected by controller 30 and as a result over and under pressure alarm conditions in the cuff will not be accurately signaled.

To insure that the pressure regulator described above responsive to the actual pressure level within cuff 2, controller 30 in the preferred embodiment includes an occlusion detector. When an occlusion of the pneumatic pathways between instrument 6 and cuff 2 is detected the occlusion detector generates an occlusion alarm signal. Controller 30 in response to the occlusion alarm signal suspends the activation of inflation valve 42 and deflation valve 48 by the pressure regulator while the occlusion alarm signal persist, this effectively prevents the pressure regulator from controlling the pressure of gas in cuff 2 at a time when the cuff pressure signal may no longer represent the actual pressure of gas in cuff 2. Controller 30 also alerts the user of instrument 6 that an occlusion exists between instrument 6 and cuff 2 by the activation of visual alarm indicator 28, the generation of audible tones and text messages shown on display panel 24, so that the user may take appropriate action to remedy the occlusion.

The occlusion detector operates by periodically transmitting a pneumatic pulse formed by the brief opening of inflation valve 42. The pneumatic pulse propagates through the pneumatic circuit formed by manifold 46; flexible plastic tubing 20, connectors 16 and 12, cuff port 8, the inflatable portion of cuff 2, cuff port 10, connectors 14 and 18, flexible plastic tubing 22 and tubing 52 to transducer 50 where it is detected. If the transmitted pneumatic pulse is not detected by transducer 50 an occlusion or other discontinuity in the pneumatic circuit between inflation valve 42 and transducer 50 exists. In the preferred embodiment the pneumatic pulse is generated by the opening of inflation valve 42, it will be obvious that a pneumatic pulse could also be formed by the opening of deflation valve 48 or that separate additional components could be used for pneumatic pulse generation and detection.

In the preferred embodiment the occlusion detector operates as described below. At regular predetermined occlusion detection cycle time intervals of 12 seconds, an occlusion detection cycle is commenced. During an occlusion detection time period the occlusion detection cycle proceeds as follows: normal operation the pressure regulator is suspended by temporarily inhibiting the activations of inflation valve 42 and deflation valve 48 by the pressure regulator; after an initial predetermined delay period of 80 ms to allow the gas pressure in the pneumatic system to stabilize, a pneumatic pressure pulse is introduced into the system by the brief activation of inflation valve 42 for a pneumatic pulse interval time while the cuff pressure signal is monitored by controller 30 for a predetermined pulse detection time interval of 120 ms, to detect the pressure fluctuations from the pressure pulse generated by the opening of inflation valve 42; at the end of the pulse detection time interval the occlusion detection cycle completes and the normal operation the pressure regulator is resumed. For clarity, the occlusion detection time period is the total time during which pressure regulation is suspended and is equal to the sum of the pulse detection time interval which includes the pulse interval time and the stabilization delay time.

When a patent pneumatic pathway exists between transducer 50 and inflation valve 42 the pneumatic pressure pulse generated by the brief activation of inflation valve 42 for the pneumatic pulse interval time is detected by transducer 50 and controller 30. If the pneumatic pulse is not detected by transducer 50 and controller 30 within the pulse detection time interval, controller 30 generates an occlusion alarm signal. As described above the user of instrument 6 is alerted to the presence of the occlusion alarm signal by the activation of visual alarm indicator 28, the generation of audible tones by speaker 54 and text messages shown on display panel 24. The activation of valves 42 and 48 by the regulation algorithm are inhibited while the occlusion alarm signal persists.

In the preferred embodiment, occlusion detection cycle time intervals of 12 seconds are employed. It will be obvious that other values for the occlusion detection cycle time interval could be readily employed. The time required to complete an occlusion detection cycle is short (200 ms) and occlusion detection cycles have no significant effect on the pressure regulator's ability to adequately control the pressure of gas with in cuff 2, therefore shorter occlusion detection cycle time intervals could be selected. Alternatively, longer occlusion detection cycle time intervals could be selected to conserve power.

In clinical use, many different sizes of cuff 2 may be optionally used with instrument 6 to accommodate different physical sizes of patients and patient limbs. The inflatable portion of a cuff suitable for application to an adult patient's thigh will have many times the volume of the inflatable portion of a cuff suitable for application to pediatric patent limbs. The volume and compliance of cuff 2 effects the degree to which the pneumatic pulse generated for occlusion detection is attenuated as it propagates through the pneumatic circuit described above.

The magnitude of the pneumatic pulse introduced into the pneumatic circuit for occlusion detection by the opening of inflation valve 42 is proportional to the pneumatic pulse interval time. The longer the duration of the pulse interval time, the longer the opening time of inflation valve 42 and the greater the magnitude of the pneumatic pulse introduced into the system.

In the preferred embodiment, it is desirable to select a value for the pneumatic pulse interval time that is optimally determined for the physical size, volume and compliance of the specific cuff connected to instrument 6. The optimal value for the pneumatic pulse interval time is the minimum valve opening time required to produce a pneumatic pulse that is reliably detectable by pressure transducer 50 and controller 30 and that the additional volume of gas added to cuff 2 from the pressure pulse has negligible effect (less than 1 mmHg) on the average gas pressure in cuff 2.

A pneumatic pulse interval time that is of sufficient time duration to produce a pneumatic pulse that is detectable when a large volume cuff such as may be applied to a patient's thigh is connected to instrument 6 would produce too great a pressure variation in a small cuff such as those used for pediatric patients.

When inflation of cuff 2 is initiated by a user of instrument 6 depressing the "inflate" key on keypad 26, controller 30 sets the pneumatic pulse interval time to an initial predetermined value of 10 ms. It will be obvious to those skilled in the art that the predetermined time interval chosen for an initial pulse interval time is a function of the design of inflation valve 42, transducer 50 and controller 30, and the characteristics of the pneumatic system employed in the preferred embodiment and that different times may be chosen for alternate hardware configurations.

Immediately after cuff inflation is completed and the pressure in cuff 2 is near the cuff pressure reference level set by the user, an optimal value for the pneumatic pulse interval time is determined by controller 30. Determination of the optimal pneumatic pulse interval time proceeds as follows.

An occlusion detection cycle is initiated as described above using the initial occlusion pulse interval time value. If the pneumatic pulse detected by transducer 50 and controller 30 exceeds a predetermined minimum pulse magnitude level, the occlusion pulse interval time is set to the initial value for all subsequent occlusion detection cycles. If the pneumatic pulse is not detected or the detected pulse is below the predetermined pulse magnitude level, the value of the pneumatic pulse interval is increased by 2 ms and another occlusion detection cycle is initiated.

This process repeats with the pneumatic pulse interval time incrementing by 2 ms each cycle, until a pneumatic pulse interval is found that produces a detectable pneumatic pulse with a magnitude greater than the minimum pulse magnitude level or the occlusion pulse interval time exceeds a predetermined maximum interval time of 30 ms. When a pneumatic pulse interval time is found that produces detectable pulses, the determination of the optimal pneumatic pulse interval time is complete and the current pneumatic interval time is used for all subsequent occlusion detection cycles while cuff 2 remains inflated. If during the optimal pneumatic pulse interval determination process the predetermined maximum interval time of 30 ms exceeded controller 30 produces an occlusion alarm signal, and operates as described above to alert the user and inhibit activation of inflation valve 42 and deflation valve 48 by the regulation algorithm.

To enable a better understanding of the invention its operation in clinical use is described below. An operator of instrument 6 will select an appropriately sized cuff 2 for application to patient limb 4 and secure cuff 2 around patient limb 4. Pneumatic passageways from instrument 6 to the inflatable portion of cuff 2 are completed by mating connectors 16 and 12, and connectors 18 and 14.

Using keypad 28 and display panel 26 the operator will then select a cuff pressure reference level for the pressure of gas to be maintained in cuff 2 during the surgical procedure when it is inflated. The inflation of cuff 2 to near the selected cuff pressure reference level will be initiated by the operator depressing the "inflate" key on keypad 28. When inflation of cuff 2 is complete as indicated by the pressure of gas in cuff 2 being near the selected cuff pressure reference level, the occlusion detector will determine the optimum pneumatic pulse magnitude to be used for occlusion detection.

The occlusion detector performs multiple occlusion detection cycles as described above, while increasing the pneumatic pulse amplitude, until the minimum pulse amplitude for reliable pulse detection is determined. The pressure regulator will operate to maintain the pressure of gas within cuff 2 near the selected cuff pressure reference level. The cuff pressure reference level may by adjusted and set to a new level at any time by the operator of instrument 6 or by controller 30 in response to changes in physiologic parameters monitored via physiologic interface 56. The occlusion detector periodically checks the pneumatic circuit formed by the inflatable portion of cuff 2 its ports and pneumatic connections to instrument 6 for occlusion of the pneumatic circuit. If the pneumatic circuit becomes occluded, the occlusion detector generates an alarm signal to alert the operator that an occlusion exists and suspends the normal operation of the cuff pressure regulator while the occlusion persists.

At the completion of the surgical procedure, the operator will initiate the deflation of cuff 2 by activating the deflate key on keypad 28. Cuff 2 may be disconnected from instrument 6 by releasing connectors 16 and 12, and releasing connectors 18 and 14. Cuff 2 may then be removed from the patient.

We claim:

1. A dual-port surgical tourniquet system having an occlusion detector, comprising:
    a tourniquet cuff for encircling a patient's limb and including an inflatable portion that communicates pneumatically with a first cuff port and that communicates pneumatically with a second cuff port independently of the first cuff port;
    a tourniquet instrument that is separately connectable to the first and second cuff ports to establish separate first and second pneumatic passageways between the tourniquet cuff and the tourniquet instrument, wherein the tourniquet instrument includes
        pressure sensing means for producing an indication of the pressure in the inflatable portion of the cuff,
        pressurizing means for pressurizing the cuff,
        pressure relief means for depressurizing the cuff,
        pressure regulation means responsive to the pressure sensing means for selectably activating the pressurizing means and the pressure relief means to regulate the pressure in the cuff near a reference pressure level during a time period suitably long for the performance of a surgical procedure; and
        an occlusion detector means for introducing a pressure pulse into the first passageway during an occlusion detection time period, and for directing the pressure pulse through the inflatable portion and into the second pneumatic passageway and for monitoring the pressure in the second passageway during the occlusion detection time period, and for producing an occlusion alarm if a fluctuation of pressure in the second passageway that is attributable to the pressure pulse is not detected within the occlusion detection time period.

2. The apparatus as defined in claim 1 wherein the occlusion detector further suspends the operation of the pressure regulation means during the occlusion detection time period.

3. The apparatus as defined in claim 1 wherein, at the commencement of the occlusion detector time period, the occlusion detector means incrementally increases the level of the pressure pulse introduced into the first pneumatic passageway from an initial level to a level that causes the fluctuation of pressure detected in the second pneumatic passageway to be greater than a predetermined minimum pressure fluctuation level.

4. The apparatus as defined in claim 1 wherein the pressure pulse differs from the reference pressure level by at least a predetermined difference pressure for a period of time less than the occlusion detection time period.

5. The apparatus as defined in claim 1 wherein the pressurizing means communicates pneumatically with the first pneumatic passageway, wherein the pressure relief means communicates pneumatically with the second pneumatic passageway, and wherein the occlusion detector means activates the pressurizing means to introduce the pressure pulse at a predetermined pressure level that is greater than the reference pressure level.

6. The apparatus as defined in claim 1 wherein the pressurize relief means communicates pneumatically with the first pneumatic passageway, wherein the pressurizing means communicates pneumatically with the second pneumatic passageway, and wherein the occlusion detector means activates the pressure relief means to introduce the pressure pulse at a predetermined pressure level that is less than the reference pressure level.

7. An occlusion detector for a dual-port surgical tourniquet cuff, comprising:
    a tourniquet cuff having an inflatable portion and adapted for encircling a patient's limb and being pressurized to a reference pressure level sufficient to stop arterial blood flow into the limb past the encircling cuff to facilitate the performance of a surgical procedure, wherein the inflatable portion communicates pneumatically with a first cuff port and a second cuff port; and
    an occlusion detector releasably connectable to the first cuff port for introducing a pneumatic pressure pulse into the first cuff port, so that the pulse moves into the inflatable portion and out of the inflatable portion into the second cuff port during an occlusion detection time period, the occlusion detector being releasably connectable to the second cuff port for monitoring the pressure at the second cuff port during the occlusion detection time period, and wherein the occlusion detector produces an occlusion alarm if a fluctuation of pressure at the second cuff port that is attributable to the pressure pulse is not detected within the occlusion detection time period.

8. The apparatus as defined in claim 7 and including tourniquet pressure regulating means communicating pneumatically with the first and second cuff ports for regulating the pressure in the tourniquet cuff near the reference pressure level, wherein the occlusion detector further suspends the regulation of the pressure by the pressure regulation means for the occlusion detection time period.

9. The apparatus as defined in claim 7 wherein the pressure pulse differs from the reference pressure level by at least a predetermined difference pressure for a period of time less than the occlusion detection time period.

10. A method for detecting an occlusion in a dual-port surgical tourniquet cuff comprising the steps of
    introducing a pneumatic pressure pulse into a first cuff port communicating pneumatically with an inflatable portion of a tourniquet cuff during an occlusion detection time period,
    directing the pressure pulse through the inflatable portion and into a separate, second cuff port that communicates pneumatic with the inflatable portion;

monitoring during the occlusion detection time period the pressure at the second cuff port to detect a fluctuation of pressure within the second cuff port, and producing an occlusion alarm if a fluctuation of pressure within the second cuff port that is attributable to the pressure pulse is not detected within the occlusion detection time period.

11. The method of claim 10 and including the step of suspending any regulation of the pressure in the inflatable portion of the tourniquet cuff by a tourniquet instrument for the duration of the occlusion detection time period.

* * * * *